US007233687B2

(12) United States Patent
Ashton

(10) Patent No.: US 7,233,687 B2
(45) Date of Patent: Jun. 19, 2007

(54) SYSTEM AND METHOD FOR IDENTIFYING OPTIMIZED BLOOD SIGNAL IN MEDICAL IMAGES TO ELIMINATE FLOW ARTIFACTS

(75) Inventor: Edward Ashton, Webster, NY (US)

(73) Assignee: VirtualScopics LLC, Rochester, NY (US)

( * ) Notice: Subject to any disclaimer, the term of this patent is extended or adjusted under 35 U.S.C. 154(b) by 70 days.

(21) Appl. No.: 10/811,887

(22) Filed: Mar. 30, 2004

(65) Prior Publication Data
US 2005/0228269 A1 Oct. 13, 2005

(51) Int. Cl.
G06K 9/00 (2006.01)
A61B 5/05 (2006.01)

(52) U.S. Cl. ........................ 382/128; 600/420
(58) Field of Classification Search ................ 600/425, 600/421, 420, 419, 431; 382/128–133; 324/309; 250/302, 303
See application file for complete search history.

(56) References Cited

U.S. PATENT DOCUMENTS

| 5,329,478 | A | * | 7/1994 | Kirk et al. ................. 708/822 |
| 5,685,305 | A | * | 11/1997 | Moonen et al. ............. 600/419 |
| 6,112,112 | A | * | 8/2000 | Gilhuijs et al. ............. 600/425 |
| 6,195,445 | B1 | * | 2/2001 | Dubuisson-Jolly et al. . 382/107 |
| 6,496,560 | B1 | * | 12/2002 | Lin et al. ...................... 378/62 |
| 6,512,807 | B1 | * | 1/2003 | Pohlman et al. ............... 378/4 |
| 6,546,275 | B2 | * | 4/2003 | Carroll ....................... 600/419 |
| 6,587,707 | B2 | * | 7/2003 | Nehrke et al. .............. 600/410 |
| 6,745,066 | B1 | * | 6/2004 | Lin et al. .................... 600/425 |
| 6,898,453 | B2 | * | 5/2005 | Lee ............................. 600/407 |
| 2004/0019267 | A1 | * | 1/2004 | Paragios et al. ............ 600/407 |
| 2004/0242994 | A1 | * | 12/2004 | Brady et al. ................ 600/420 |
| 2005/0033159 | A1 | * | 2/2005 | Mistretta et al. ........... 600/420 |

OTHER PUBLICATIONS

Mark Rijpkema, et al. "Method for Quantitative Mapping of Dynamic MRI Contrast Agent Uptake In Human Tumors", Journal of Magnetic Resonance Imaging 14:457-463, 2001, pp. 457-463.

* cited by examiner

Primary Examiner—Brian L. Casler
Assistant Examiner—Jennifer Horwat
(74) Attorney, Agent, or Firm—Blank Rome LLP

(57) ABSTRACT

In a sequence of medical image data showing tumors and blood vessels, a plasma signal is optimized to avoid flow artifacts by receiving a user input of a blood region and using the user input to seed an automated search. Each voxel is scored by time point of maximum intake, slope at maximum intake, peak value and conformance to a gamma variate curve, and the voxels with the highest scores are included in the ideal plasma region of interest. Uptake curves for both tumors and plasma are determined and used to estimate a volume transfer constant.

28 Claims, 8 Drawing Sheets

SYSTEM AND METHOD FOR IDENTIFYING OPTIMIZED BLOOD SIGNAL IN MEDICAL IMAGES TO ELIMINATE FLOW ARTIFACTS

FIELD OF THE INVENTION

The present invention is directed to the identification of blood signals in medical images, such as magnetic resonance (MR) images, and more particularly to such identification which overcomes the corruption of such signals by arterial flow artifacts.

DESCRIPTION OF RELATED ART

Dynamic contrast enhanced MRI (dceMRI) has demonstrated considerable utility in both diagnosing and evaluating the progression and response to treatment of malignant tumors. dceMRI involves the periodic acquisition of T1-weighted images before, during and after injection of a gadolinium labeled tracer such as gadopentetate dimeglumine. The change over time in signal intensity in a voxel or region of interest in this time series can then be related to tracer concentration. By making use of a two-compartment model, with one compartment representing blood plasma and the other abnormal extra-vascular extra-cellular space (EES), the observed uptake curves in tissue and plasma can be used to estimate various physiological parameters.

The parameter of primary interest in this work is the volume transfer constant between blood plasma and EES, commonly referred to as $K^{trans}$. This parameter is related to both blood flow and endothelial permeability, and is therefore a good endpoint for estimating the blood supply available to a target malignancy.

One of the primary challenges in estimating perfusion parameters is identifying an accurate plasma uptake curve. Using a theoretical curve ignores differences in injection rate and cardiac output, which can greatly reduce reproducibility. However, the MR signal in arteries is frequently corrupted by flow artifacts, with the result that regions of interest at different points in the same artery or in other nearby vessels can provide grossly different uptake curves.

This problem is illustrated in FIGS. 1A and 1B. In FIG. 1A, one section from subject 1, time 1, has had two small arteries identified therein as regions of interest (ROI's). The ROI's identified on the right and the left are identified as vessel 1 and vessel 2, respectively. FIG. 1B shows the raw uptake curves for vessels 1 and 2, along with a calculated ideal arterial uptake curve calculated in accordance with the present invention (to be described below).

Note that in FIG. 1B, vessel 1 and vessel 2 show significantly different uptake curves. Moreover, neither vessel shows the distinctive sharp peak and subsequent plateau characteristic of plasma enhancement following injection of a tracer bolus.

SUMMARY OF THE INVENTION

It is an object of the invention to allow the calculation of blood uptake curves with improved accuracy. It is another object of the invention to allow such calculation such that flow artifacts are eliminated.

To achieve the above and other objects, the present invention is directed to a system and method for the identification of an optimized plasma signal which is intended to eliminate this source of measurement variability and thereby increase the sensitivity to change of perfusion parameter measurements. The uptake curve according to the present invention shows a greater enhancement peak than that of either vessel, a smoother plateau, and a more characteristic shape.

The present invention allows the calculation of perfusion parameters in imaging technologies such as dynamic contrast enhanced MRI. Uptake curves are calculated for both tumor tissue and plasma. Inter-operator variability in the derived rate constant between plasma and extra-cellular extra-vascular space is assessed using semi-automated tumor margin identification with both manual and automated plasma identification. In addition, an assessment is made of the contribution to total variability made by differences in tumor margin identification and differences in plasma identification. Experimental results show a mean coefficient of variability (CV) for parameter measurement with manual plasma identification of 20.1%, with a mean CV for parameter measurement with automated plasma identification of 6.7%. Analysis shows that 67% of the variability in parameter measurement with manual plasma identification is attributable to differences in identified plasma signal, with the remainder attributable to differences in identified tumor margins.

Manual plasma identification for perfusion parameter calculation is currently standard practice for both clinical and experimental purposes. Increased accuracy and sensitivity to change can be achieved by making use of an automated method for plasma identification, as achieved by the present invention.

In some cases it may be possible to identify automatically the tumor and the artery, for example by use of special pulse sequences, pre-contrast, which create a known contrast with respect to surrounding tissue.

The present invention can be applied to a variety of imaging technologies, such as dynamic contrast enhanced CT.

The present invention bears some similarities to the algorithm presented by Rijpkama, M, Johannes, H., et al, "Method for quantitative mapping of dynamic MRI contrast agent uptake in human tumors," JMRI, pp. 457-463, 2001. However, the present invention provides automation. Also, because the method of Rijpkama et al selects most or all of the arterial voxels, it is vulnerable to the arterial flow artifacts which the present invention is intended to eliminate.

BRIEF DESCRIPTION OF THE DRAWINGS

A preferred embodiment of the present invention will be disclosed in detail with reference to the drawings, in which.

DETAILED DESCRIPTION OF THE PREFERRED EMBODIMENT

A preferred embodiment of the present invention, as well as experimental results, will now be set forth in detail with reference to the drawings.

Figure 1A:
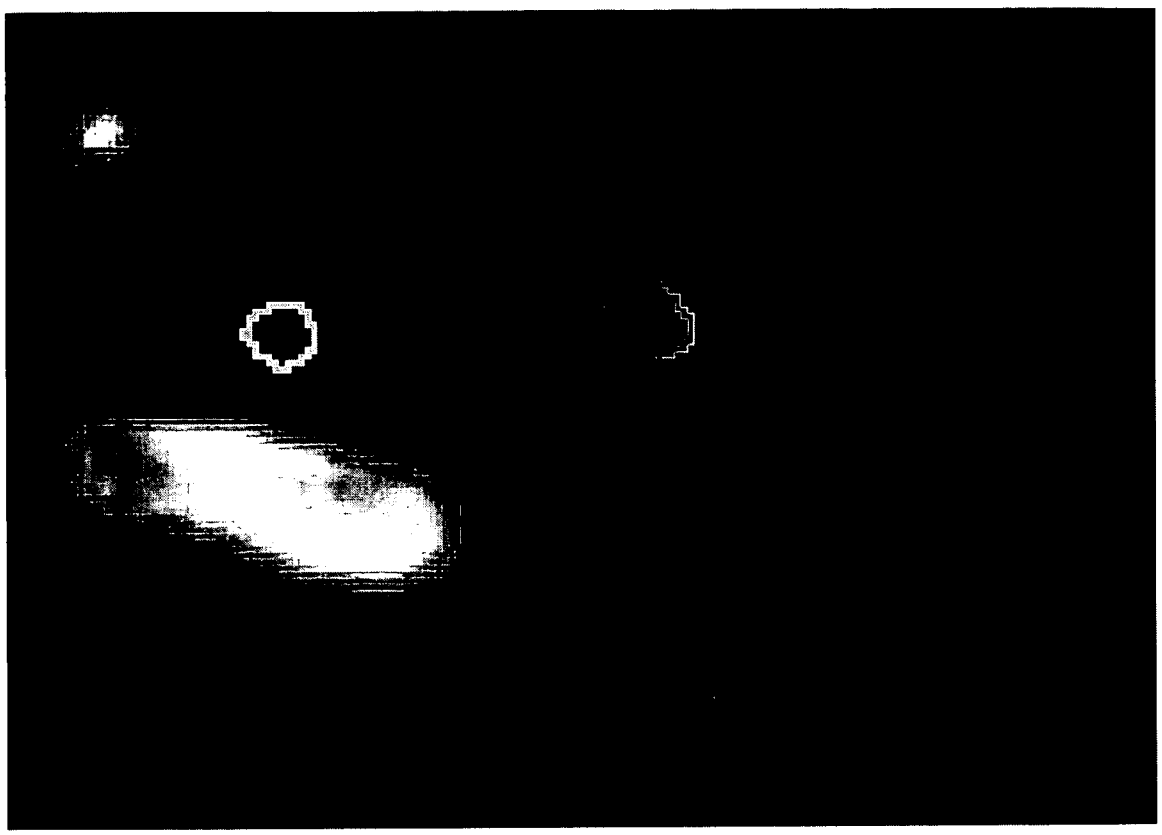
FIG. 1A is a raw image with two arteries identified therein.
Figure 1B:
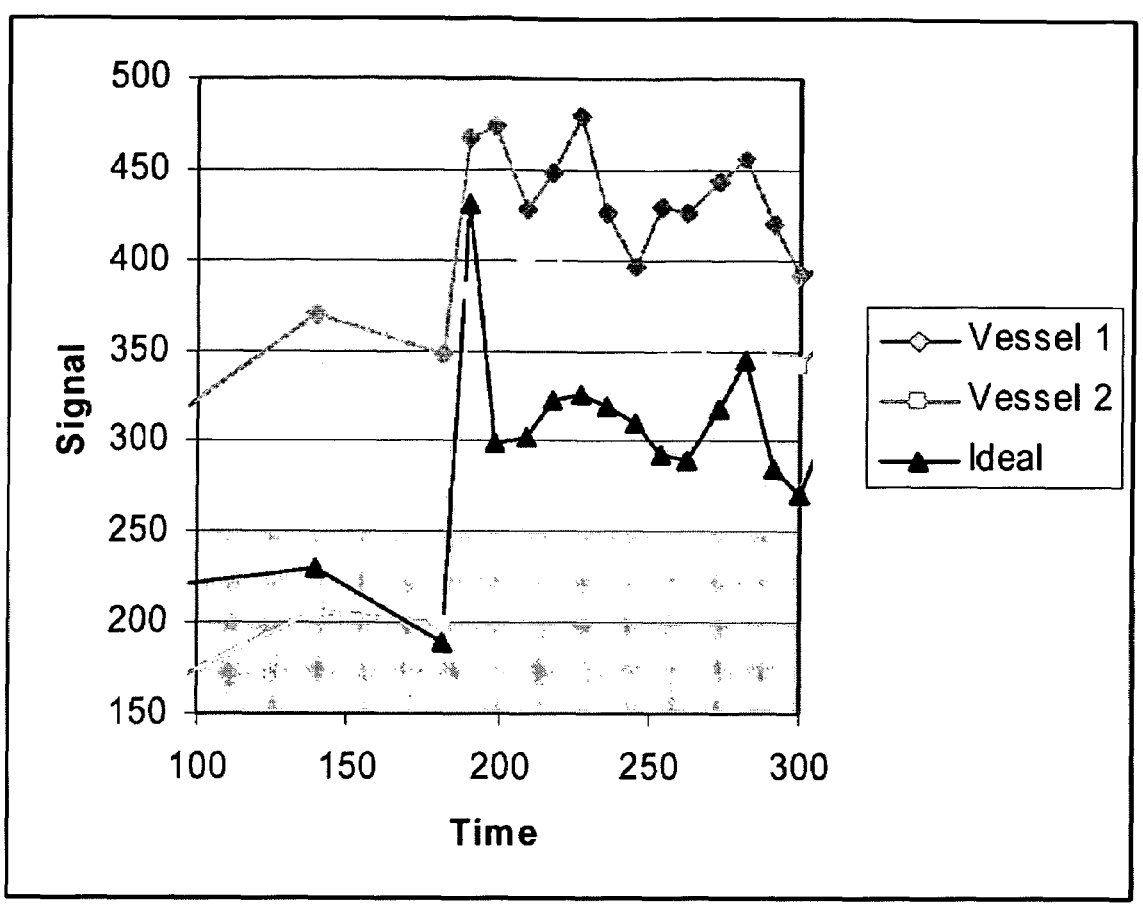
FIG. 1B is a plot of blood uptake curves from the arteries identified in FIG. 1A, as well as an optimal arterial uptake curve calculated in accordance with the preferred embodiment.
Figure 2:
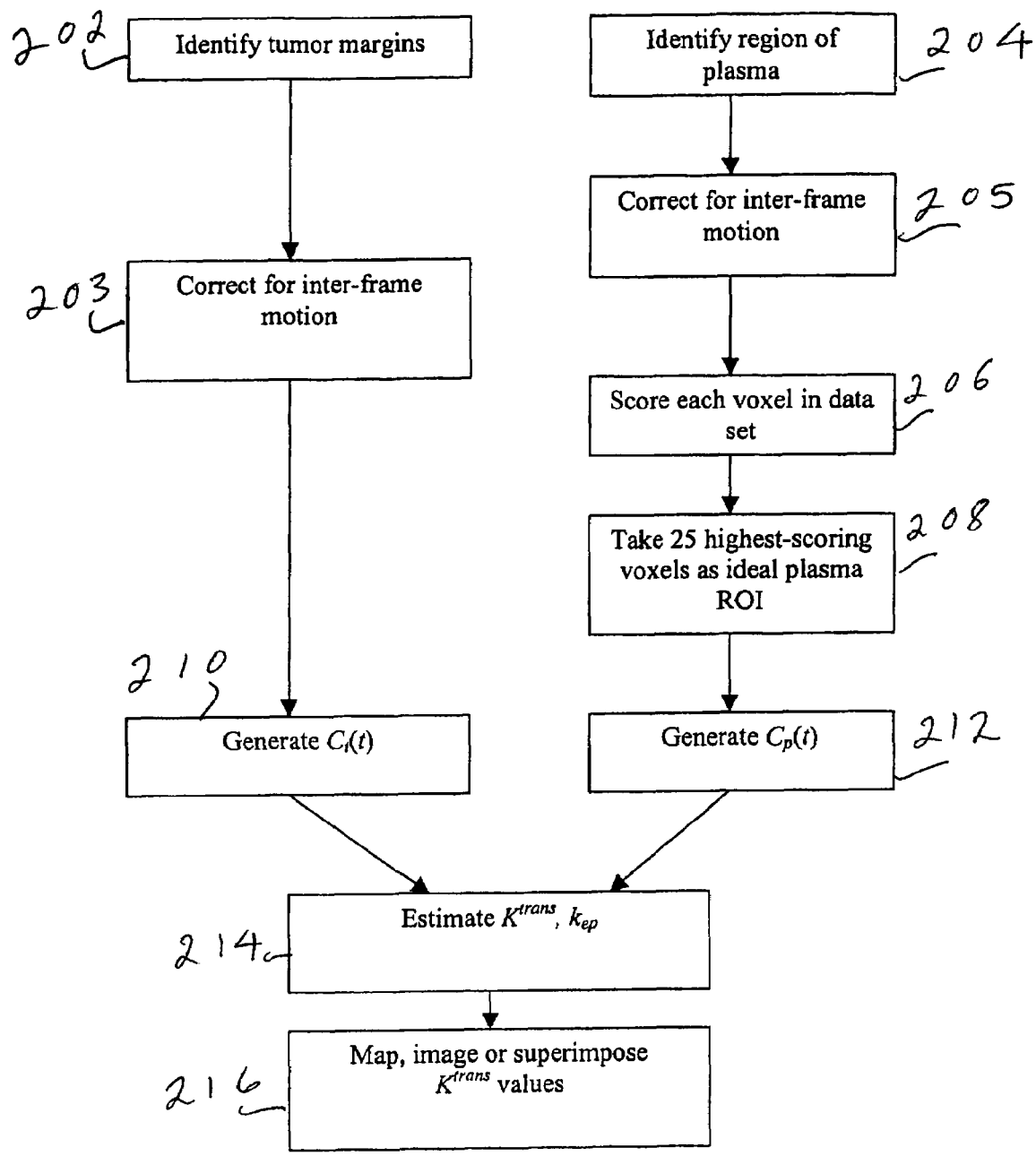
FIG. 2 is a flow chart showing the process carried out in the preferred embodiment.

The process according to the preferred embodiment will be disclosed with reference to the flow chart of FIG. 2. Tumor margins are identified in step 202 using Geometrically Constrained Region Growth (GEORG). This technique requires a user to place a seed or string of seeds within each desired structure throughout the volume using one or more mouse clicks. The seed regions then expand into neighboring voxels provided that two constraints are satisfied: the grayscale value of the neighboring voxel must have a high probability of falling within the statistical distribution defined by all currently included voxels, and inclusion of the neighboring voxel must not cause the shape of the included region to deviate excessively from the a priori regional shape model. Once initiated, the expansion process continues until a stable boundary has been established. The resulting contour is then converted into a snake which can be interactively corrected by the analyst if the initial result is sub-optimal.

Alternatively, step 202 could be performed by automatic identification of the tumor and the artery. One technique for doing so is by the use of special pulse sequences, pre-contrast, which create known contrast with respect to the surrounding tissue.

After step 202, an optional step 203 of motion correction between time frames may be performed. Step 203 may be used to correct for breathing and other patient motions. Techniques for inter-frame motion correction are known in the art and will therefore not be disclosed in detail here, although their use in the context of the present invention is novel.

After identifying the tumor margins, the analyst identifies a region of plasma in step 204, preferably in an artery in close proximity to the tumor. This is done using manual tracing with a computer mouse. An alternative way to carry out step 204 is by using knowledge of the timing of the injection and the start of scanning rather than the user-identified plasma region. Similarly to step 202, step 204 may be followed by an optional step 205 of inter-frame motion correction.

At this point, the identified plasma region is used for parameter calculation, as described below. In addition, the identified plasma region is used in to initialize an automated search algorithm whose intent is to identify an optimized plasma signal for the data set under consideration. Each voxel in the data set is assigned a score in step 206 based on time point of maximum uptake, slope at maximum uptake, peak value, and conformance to a gamma variate curve. The highest scoring twenty-five voxels in the data set are then assigned in step 208 to the ideal plasma region of interest. Thus, an optimized plasma signal is derived, the signal being optimized to eliminate flow artifacts.

After plasma has been identified by either manual or automated means, uptake curves are generated for both tumor and plasma in steps 210 and 212, respectively. These are designated $C_t(t)$ and $C_p(t)$, respectively. In the interests of noise reduction, both plasma and tumor data are fit to gamma variate curves. The vascular bed is modeled as a linear system, such that:

$$C_t(t)=C_p(t)*h(t) \tag{1}$$

with impulse response h(t) given by:

$$h(t)=K^{trans}e^{-k_{ep}t} \tag{2}$$

where $k_{ep}$ is the rate constant between the EES and blood plasma. Given $C_t(t)$ and $C_p(t)$, $K^{trans}$ and $k_{ep}$ are estimated in step 214 using a gradient-descent energy minimization scheme. Local minima are avoided through the use of multiple instantiations with different initial parameter settings. In step 216, the $K^{trans}$ values can be mapped or imaged, or they can be superimposed on one of the original scan planes, so that the user can view the higher and lower $K^{trans}$ values within the tumor.

Experimental results will now be presented. The experiments involved in this study were intended to assess the reproducibility of perfusion measurements using manual and automated plasma identification, and to determine the percentage of measurement variability due to differences in tumor margin and plasma region of interest, respectively. Experimental data were derived from three dogs with naturally occurring mammary tumors. Each animal was imaged three times over a period of 12 weeks. Images for this study were acquired using a GE 1.5T LX/CV scanner. Three slices through each tumor were acquired using a cardiac coil. Perfusion images used a GRE pulse sequence with a repetition time of 20 ms, echo time of 1 ms, and a flip angle of 40 degrees. Imaging time for each image set was seven seconds, with a two second scanner delay, yielding temporal resolution for the data set of nine seconds. The reconstruction matrix was 256×192, FOV was 140 mm, and slice thickness was 4 mm.

Figure 3:
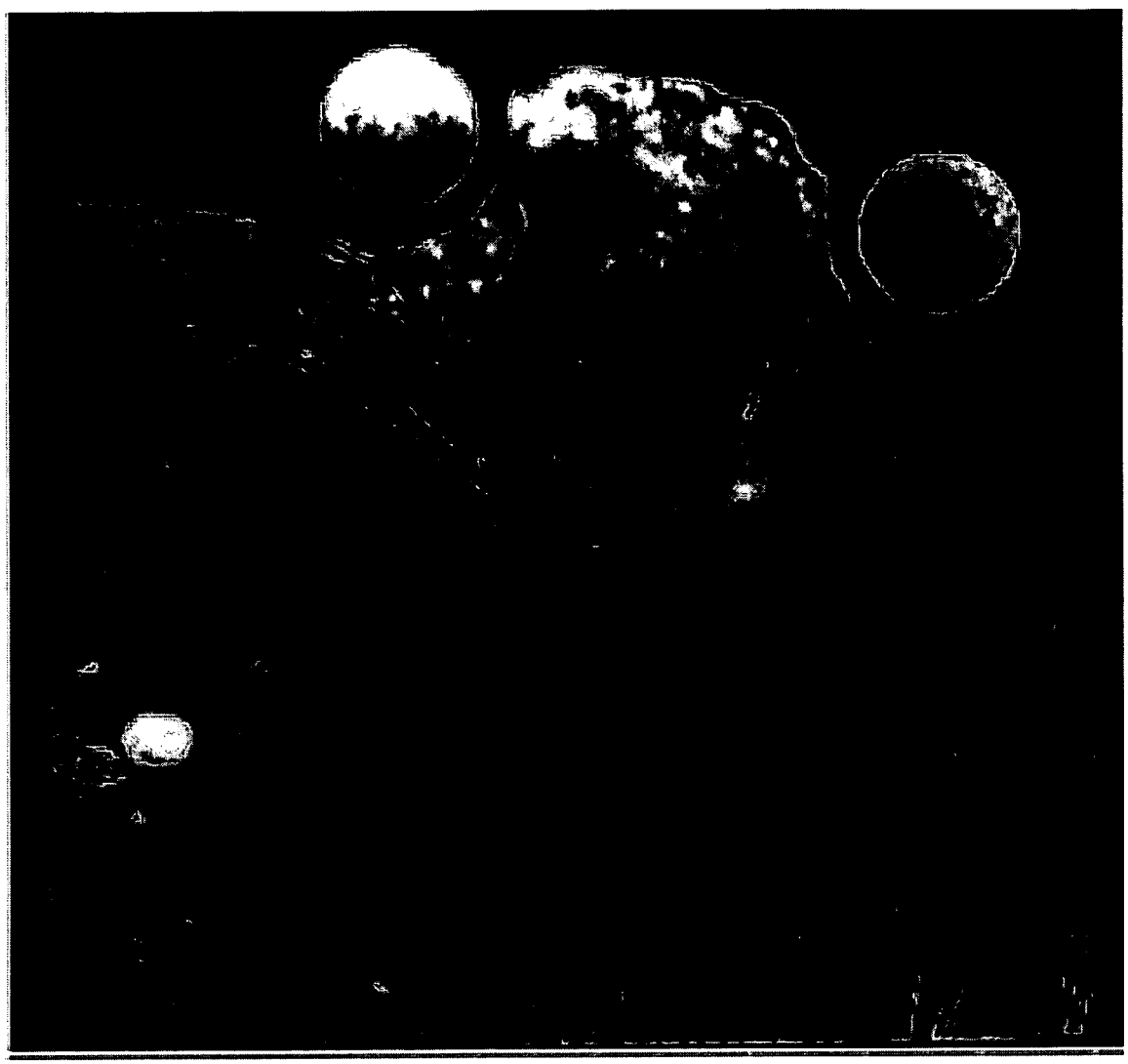
FIG. 3 is a sample image from a perfusion data set used to test the preferred embodiment.

FIG. 3 shows a sample image from the perfusion data set for Subject 1 at Time 3. The circles on either side of the tumor are phantoms. These were worn on a belt around the animal during imaging and were used for motion estimation and correction.

Because a primary aim of the testing of the preferred embodiment was the assessment of inter-operator variability, four analysts were trained in the use of the analysis software. All analysts were also trained in the appearance of canine mammary tumors and the selection of appropriate plasma regions using images from animals not included in this study. Each analyst was then asked to identify and delineate both tumor and plasma in each of the nine included data sets. When identifying plasma, the analysts had the option to view the uptake curve for the currently selected region at any time, and to erase, modify or replace the currently selected region. In this way each analyst was able to manually select a reasonably optimized plasma region.

Once all regions of interest were delineated, $K^{trans}$ values were calculated first using the regions of interest as identified by the analyst, and then using the analyst's tumor identification with the automatically identified plasma uptake curve. By comparing the variance seen between analysts using manually identified plasma with that seen between analysts using the automatically identified plasma, which was identical across analysts, it was possible to isolate variability related to plasma signal from that related to differences in tumor margin identification.

Coefficients of variability in measurement of $K^{trans}$ among the four analysts, defined as measurement standard deviation divided by measurement mean, were calculated separately for manual and automatic plasma identification, and for each of the nine cases examined. For the nine manual plasma identifications, coefficients of variability ranged from 3.1% to 39.2%, with a mean of 20.1% and a median value of 21.5%. For the nine automated plasma identifications, coefficients of variability ranged from 3.1% to 11.8%, with a mean of 6.7% and a median value of 6.2%.

Bearing in mind that the same tumor margins were used for both the automated and the manual plasma calculations, it can be generally surmised that approximately two-thirds of the variability seen in the manual measurements was a result of differing plasma signal identifications, with the remaining one-third attributable to differing tumor margin identifications. It should be noted that the variability attributed to differences in tumor margins is similar to that reported previously for volume measurements of lung tumors using GEORG.

Figure 4:
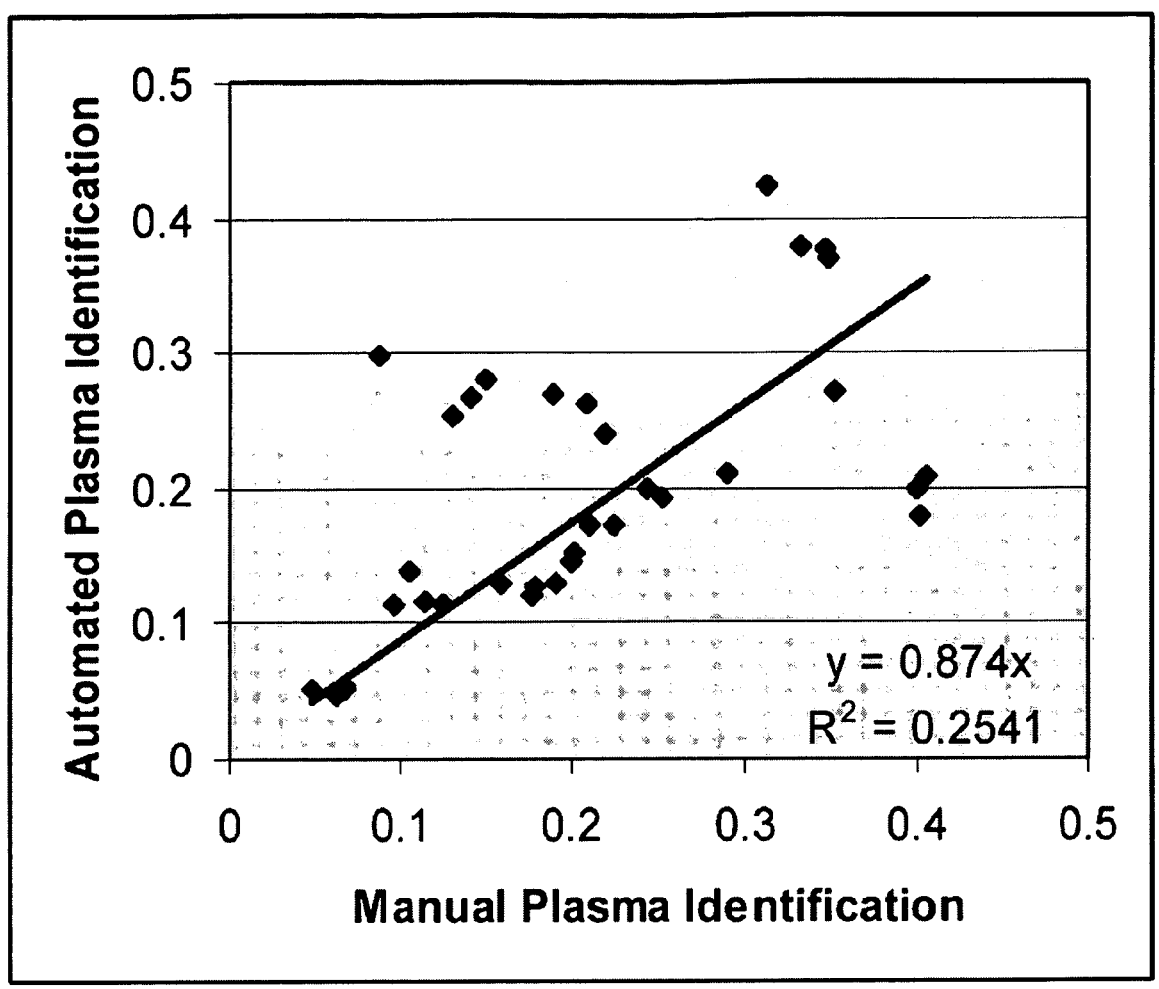
FIG. 4 is a scatterplot of $K^{trans}$ values using manual and automatic plasma identification.

An examination of a scatterplot of $K^{trans}$ measurements using manual vs. automatic plasma identification, as shown in FIG. 4, shows that the correlation between the two measures is reasonable given the high variability of the manual measurements. It also shows a slope of 0.874, indicating that on average the manual measurement gives a somewhat higher estimation of $K^{trans}$ than the automatic measurement. This is as expected, since the general effect of flow artifacts will be to reduce the apparent plasma enhancement, thereby exaggerating the proportion of tracer apparently passing into the EES.

Figure 5:
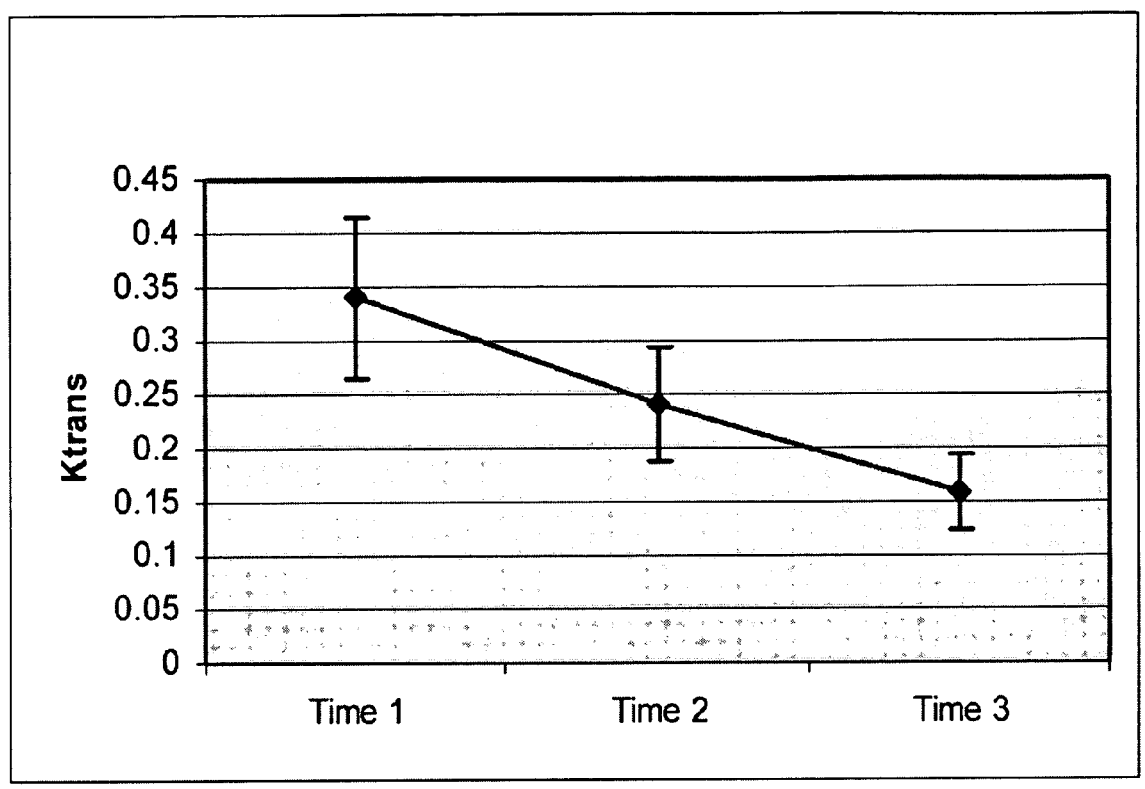
FIG. 5 is a trend line using manual plasma identification for a subject.

FIG. 5 shows a trend line of $K^{trans}$ using manual plasma identification for subject 1. The subject cannot be confidently classified as declining until time 3.

Figure 6:
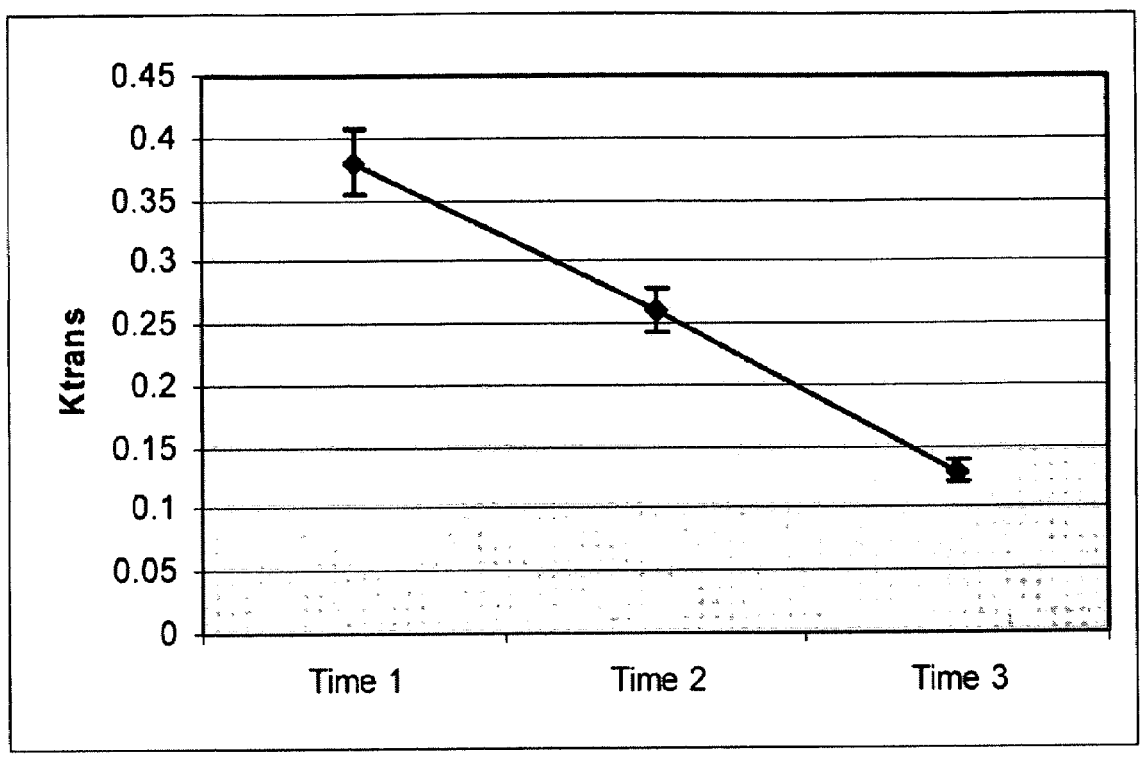
FIG. 6 is a trend line using automated plasma identification for the same subject.

FIG. 6 shows a trend line of $K^{trans}$ using automated plasma identifcation for subject 1. The subject can be confidently classified as declining after time 2.

An examination of the trend over time in $K^{trans}$ for subject 1 using manual and automated plasma identification, as shown in FIGS. 5 and 6, highlights the value of the reduced measurement variability afforded by the automated process. Although both trend lines indicate that vascular perfusion for this tumor is declining over time, higher variability makes that assumption statistically insupportable at time two for manual plasma identification, and marginally supportable after time three. Using automated plasma identification, however, this subject may be confidently classified as declining after time 2.

The difficulty of identifying a suitable plasma signal is typically greater in smaller animals such as the dogs used in study than in humans. This is due to small animals' higher blood velocity, which exaggerates flow artifacts in the arteries, as well as to the lower signal to noise ratio that is achievable when imaging smaller anatomy. The values given above for parameter variability due to differences in plasma identification should be considered an upper limit when estimating likely variability in human studies.

Figure 7:
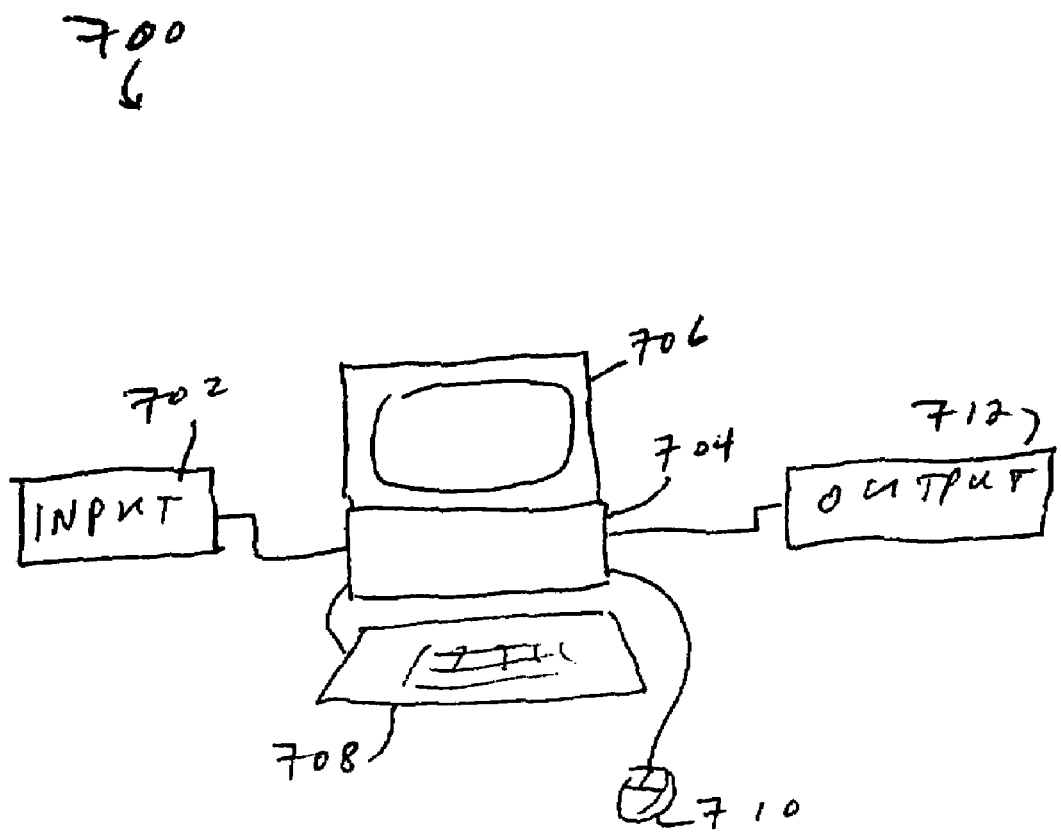
FIG. 7 is a block diagram of a system on which the preferred embodiment can be implemented.

The preferred embodiment, as well as other embodiments, can be implemented on hardware such as the system 700 shown in FIG. 7. An input 702 receives image data, which can be previously stored, received from an imaging device, or communicated from a remote location. A CPU 704 receives the imaging data from the input and performs the operations disclosed above. The CPU interfaces with the analyst through a display 706, a keyboard 708 and a mouse or other pointing device 710; the utility of the mouse 710 for identifying seeds and regions has been disclosed above. The results can be output to any suitable output 712, e.g., a printer, a storage device, or a communication device for communicating the results to a remote location.

While a preferred embodiment of the present invention has been set forth above, those skilled in the art who have reviewed the present disclosure will readily appreciate that other embodiments can be realized within the scope of the present invention. For example, the utility of the present invention is not limited to MRI. Also, any suitable hardware could be used; for example, instead of a mouse, a light pen, stylus and pressure pad, or other suitable pointing device could be used. Furthermore, any suitable technique for identifying tumor margins could be used. Therefore, the present invention should be construed as limited only by the appended claims.

I claim:

1. A method for identifying an ideal plasma region of interest in a series of medical images, the ideal plasma region of interest being a region which is optimized to eliminate flow artifacts in a signal from the ideal plasma region of interest, the method comprising:
    (a) receiving image data representing the series of medical images into a computing device;
    (b) receiving an identification of a plasma region;
    (c) automatically assigning a score to each voxel in the image data in accordance with suitability for inclusion in the ideal plasma region of interest;
    (d) identifying the ideal plasma region of interest as including a plurality of voxels whose scores as assigned in step (c) are highest; and
    (e) using the signal from the ideal plasma region of interest to perform a diagnosis.

2. The method of claim 1, wherein step (c) comprises, for each voxel:
    (i) determining a time point of maximum uptake, a slope at maximum uptake, a peak value and conformance to a gamma variate curve; and
    (ii) assigning the score in accordance with step (c)(i).

3. The method of claim 1, wherein step (b) comprises receiving a manual identification of the plasma region from a user into the computing device.

4. The method of claim 1, wherein the identification of the plasma region is determined from a time of contrast injection in the medical images and a start of scanning of the medical images.

5. A device for identifying an ideal plasma region of interest in a series of medical images, the ideal plasma region of interest being a region which is optimized to eliminate flow artifacts in a signal from the ideal plasma region of interest, the device comprising:
    an input for receiving image data representing the series of medical images;
    a region identifying device for providing an identification of regions in the image data; and
    "a computing device, in communication with the input and the region identifying device, programmed for receiving an identification of a plasma region from the region identifying device, automatically assigning a score to each voxel in the image data in accordance with suitability for inclusion in the ideal plasma region of interest, identifying the ideal plasma region of interest as including a plurality of voxels whose scores are highest, and using the signal from the ideal plasma region of interest to perform a diagnosis."

6. The device of claim 5, wherein, for each voxel, the computing device determines a time point of maximum uptake, a slope at maximum uptake, a peak value and conformance to a gamma variate curve, and assigns the score in accordance with the time point of maximum uptake, the slope at maximum uptake, the peak value and the conformance to the gamma variate curve.

7. The device of claim 5, wherein the region identifying device comprises a pointing device for allowing a user to identify the regions in the series of medical images.

8. The device of claim 5, wherein the region identifying device determines the identification of the plasma region from a time of contrast injection in the medical images and a start of scanning of the medical images.

9. A method for estimating a volume transfer constant between blood plasma and extra-vascular extra-cellular space in a series of medical images, the method comprising:
   (a) receiving image data representing the series of medial images into a computing device;
   (b) identifying tumor margins in the image data;
   (c) automatically identifying an optimized plasma signal in the image data such that the optimized plasma signal is optimized to eliminate flow artifacts;
   (d) determining uptake curves from the image data in accordance with both the tumor margins and the optimized plasma signal; and
   (e) estimating the volume transfer constant from the uptake curves determined in step (d).

10. The method of claim 9, wherein step (c) comprises:
   (i) receiving an identification of a plasma region;
   (ii) automatically assigning a score to each voxel in the image data in accordance with suitability for inclusion in the ideal plasma region of interest; and
   (iii) identifying the ideal plasma region of interest as including a plurality of voxels whose scores as assigned in step (c)(ii) are highest.

11. The method of claim 10, wherein step (c)(i) comprises receiving a manual identification of the plasma region from a user into the computing device.

12. The method of claim 10, wherein step (c)(i) comprises determining the identification of the plasma region from a time of contrast injection in the medical images and a start of scanning of the medical images.

13. The method of claim 10, wherein step (c)(ii) comprises, for each voxel:
   (A) determining a time point of maximum uptake, a slope at maximum uptake, a peak value and conformance to a gamma variate curve; and
   (B) assigning the score in accordance with step (c)(ii)(A).

14. The method of claim 10, wherein step (b) is performed through geometrically constrained region growth.

15. The method of claim 10, wherein step (e) comprises estimating the volume transfer constant through gradient-descent energy minimization.

16. The method of claim 15, wherein the gradient-descent energy minimization is performed a plurality of times to avoid local minima.

17. The method of claim 9, further comprising (f) forming an image representing the volume transfer constant.

18. The method of claim 9, wherein at least one of step (b) and step (c) comprises correcting for inter-frame motion.

19. A device for estimating a volume transfer constant between blood plasma and extra-vascular extra-cellular space in a series of medical images, the device comprising:
   an input for receiving image data representing the series of medical images;
   a pointing device for allowing a user to identify regions in the series of medical images; and
   a computing device, in communication with the input and the pointing device, programmed for identifying tumor margins in the image data, automatically identifying an optimized plasma signal in the image data such that the optimized plasma signal is optimized to eliminate flow artifacts, determining uptake curves from the image data in accordance with both the tumor margins and the optimized plasma signal, and estimating the volume transfer constant from the uptake curves.

20. The device of claim 19, wherein the computing device identifies the optimized plasma signal by receiving an identification of a plasma region, automatically assigning a score to each voxel in the image data in accordance with suitability for inclusion in the ideal plasma region of interest, and identifying the ideal plasma region of interest as including a plurality of voxels whose scores are highest.

21. The device of claim 20, wherein the computing device receives a manual identification of the plasma region from a user into the computing device.

22. The device of claim 20, wherein the computing device determines the identification of the plasma region from a time of contrast injection in the medical images and a start of scanning of the medical images.

23. The device of claim 20, wherein the computing device assigns the score to each voxel by determining a time point of maximum uptake, a slope at maximum uptake, a peak value and conformance to a gamma variate curve, and assigning the score in accordance with the time point of maximum uptake, the slope at maximum uptake, the peak value and the conformance to the gamma variate curve.

24. The device of claim 20, wherein the computing device identifies the tumor margins through geometrically constrained region growth.

25. The device of claim 20, wherein the computing device estimates the volume transfer constant from the uptake curves by estimating the volume transfer constant through gradient-descent energy minimization.

26. The device of claim 25, wherein the gradient-descent energy minimization is performed a plurality of times to avoid local minima.

27. The device of claim 19, wherein the computing device further forms an image representing the volume transfer constant.

28. The device of claim 19, wherein the computing device corrects at least one of the tumor margins and the plasma signal for inter-frame motion.

* * * * *